United States Patent [19]

Iriuchijima et al.

[11] Patent Number: 4,686,296
[45] Date of Patent: Aug. 11, 1987

[54] PROCESS FOR PRODUCING OXIRACETAM

[75] Inventors: Shinobu Iriuchijima; Hirohiko Kobayashi; Kyoji Aoki; Takeshi Oda, all of Tokyo; Masayuki Shinoyama; Yoshifumi Nosaka, both of Niigata, all of Japan

[73] Assignee: Denki Kagaku Kogyo Kabushiki Kaisha, Tokyo, Japan

[21] Appl. No.: 889,428

[22] Filed: Jul. 22, 1986

[30] Foreign Application Priority Data

Jul. 26, 1985 [JP] Japan .................. 60-164019
Feb. 7, 1986 [JP] Japan .................. 61-23915

[51] Int. Cl.$^4$ .......................................... C07D 207/12
[52] U.S. Cl. ............................................ 548/544
[58] Field of Search ............................... 548/544

[56] References Cited

U.S. PATENT DOCUMENTS 4,118,396 10/1978 Pifferi et al. ............. 548/544 X
4,124,594 11/1978 Monguzzi et al. ........... 548/544
4,173,569 11/1979 Banti et al. ............... 548/544
4,341,790 7/1982 Betzing et al. ............. 548/544 X

FOREIGN PATENT DOCUMENTS 0154490 9/1985 European Pat. Off. ......... 548/544
56-68644 6/1981 Japan .
57-183756 11/1982 Japan ..................... 548/544
58-22034 5/1983 Japan .
60-231651 11/1985 Japan .
60-208957 11/1985 Japan .

OTHER PUBLICATIONS

Z. Physiol. Chem., 64, pp. 348-366 (1910); Bergell et al.
J. Org. Chem., 32, pp. 3888-3994 (1967); McClure.

Primary Examiner—Joseph Paul Brust
Attorney, Agent, or Firm—Jeffers, Hoffman & Niewyk

[57] ABSTRACT

A process for producing oxiracetam (4-hydroxy-2-oxo-1-pyrrolidineacetamide) useful as an agent for improving brain metabolism, under mild conditions and in a single process is provided, this process comprises reacting glycinamide with a butyric acid ester expressed by the formula

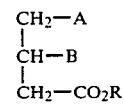

wherein A represents a halogen atom or an epoxy group, B represents hydroxyl group, but when A is an epoxy group, A and B together form an epoxy group, and R represents an alkyl group.

15 Claims, No Drawings

PROCESS FOR PRODUCING OXIRACETAM

BACKGROUND OF THE INVENTION

1. Field of the Invention

This invention relates to a process for producing oxiracetam(4-hydroxy-2-oxo-1-pyrrolidineacetamide) known as a pharmaceutical (an agent for improving brain metabolism).

2. Related Art Statement

As the process for producing oxiracetam aimed in the present invention, various processes have so far been known, such as (1) a process of obtaining it through reactions of five steps, using ethyl iminodiacetate and ethoxycarbonylacetyl chloride as raw materials (USP No. 4118396/78), (2) a process of obtaining it by using γ-amino-β-hydroxybutyric acid as raw material and adding thereto hexamethyldisilazane or the like, followed by reactions of three steps (Italian Pat. No. 20227A/1977, (3) a process of reacting a glycinamide derivative having a shielding group with a 3,4-epoxybutyric acid ester, followed by shield-removal and cyclization (Italian Pat. No. 19802A/84), and (4) a process of using diketene as starting raw material, followed by reactions of a number of steps, that is, reduction, shielding of hydroxyl group, cyclization, shield-removal, amidation (Italian Pat. No. 20358A/84).

However, any of conventional processes have such drawbacks that raw materials used are expensive and that reactions of many steps are required.

SUMMARY OF THE INVENTION

The present inventors have made extensive research in order to find a process for producing oxiracetam in a short process and through a simple reaction by the use of raw materials which are easily and commercially available at a cheap cost, and as a result, have found that when an alkyl butyrate having specified groups at γ-position and β-position is reacted with glycinamide, its salt or a mixture thereof, it is possible to produce oxiracetam in a single step.

The present invention resides in a process for producing oxiracetam which comprises reacting glycinamide with a butyric acid ester expressed by the formula (I)

$$\begin{array}{l} CH_2-A \\ | \\ CH-B \\ | \\ CH_2-CO_2R \end{array}$$

wherein A represents a halogen atom or an epoxy group, B represents hydroxyl group, but when A represents an epoxy group, A and B together form an epoxy group, and R represents an alkyl group of (1 to 4 carbon atoms).

DETAILED DESCRIPTION OF PREFERRED EMBODIMENTS

The preparation reaction of oxiracetam in the process for producing it according to the present invention may be shown as follows:

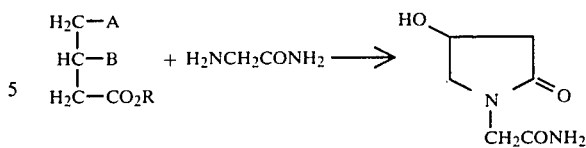

In the above reaction equation, A, B and R are as defined above.

In the above reaction, the α-amino group of glycinamide reacts with the carbon at γ-position and the ester carbonyl group of the butyric acid ester expressed by the formula (I) to form a ring, and thus oxiracetam is produced. Accordingly, A in the formula (I) is a leaving group, and a halogen atom or an epoxy group. Further, B is hydroxyl group in the case where A is a halogen atom, and B forms an epoxy group together with A in the case where A is an epoxy group. R represents an alkyl group such as methyl, ethyl, propyl, butyl, isobutyl, etc.

In the case where the alkyl butyrate expressed by the formula (I) in the present invention is e.g. 4-chloro-3-hydroxybutyric acid alkyl ester, the reaction is as follows:

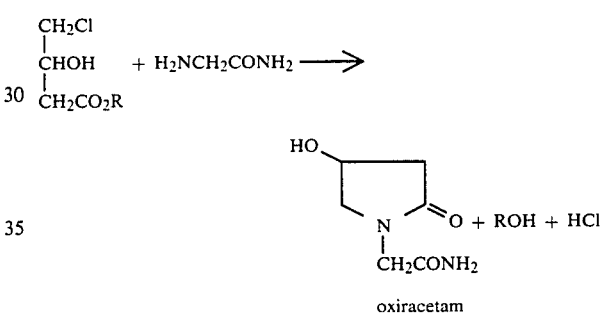

oxiracetam

4-Chloro-3-hydroxybutyric acid alkyl ester as one of the raw materials is easily prepared e.g. by carbonylation reaction of epichlorohydrin which is commercially available at a cheap cost as an industrial raw material (Japanese patent application laid-open No. Sho 56-68644/1981). Further, glycinamide or its salts as another of the raw materials are obtained e.g. by the reaction of ethyl monochloroacetate with aqueous ammonia (Z. Physiol Chem., 64, 348 (1910)).

In carrying out the above reaction, use of a solvent is preferred, and protonic solvents such as water, methanol, ethanol, propanol, butanol, 2-methoxyethanol, etc. and other solvents such as dioxane, 1,2-dimethoxyethane, diglyme, etc. and mixed solvents of the foregoing may be use, but among these, protonic solvents are preferred and particularly ethanol is preferred. Further, as the present reaction proceeds, hydrogen halide is formed, but since this hydrogen halide hinders the reaction, it is preferred to make a neutralizing agent present. As the neutralizing agent, organic or inorgainc bases are used. As the organic bases, amines such as trimethylamine, N,N-diethylaniline, glycinamide, etc., and as the inorganic bases, alkali metal or alkaline-earth metal hydroxides such as NaOH, KOH, Ca(OH)$_2$, etc. and alkali metal carbonates such as Na$_2$CO$_3$, NaHCO$_3$, K$_2$CO$_3$, etc. may be used, but in consideration of yield and economy, alkali metal carbonates are preferred and Na$_2$CO$_3$ is particularly preferred. The quantity thereof used is one equivalent relative to the 4-halo-3-hydroxybutyric acid esters, and when glycinamide is used in the form of its acid salt such as hydrochloride, it is preferred to add further one equivalent. The reaction temperature is in the range of 60° to 160° C., preferably 70° to 130° C., and the reaction time is in the range of 1 to 70 hours, depending on the temperature and other conditions. In addition, a catalytic quantity of an iodide such as KI, NaI, etc. promotes the present reaction.

Further, when the butyric acid alkyl ester expressed by the formula (I) is e.g. a 3,4-epoxybutyric acid alkyl ester, the reaction is as follows:

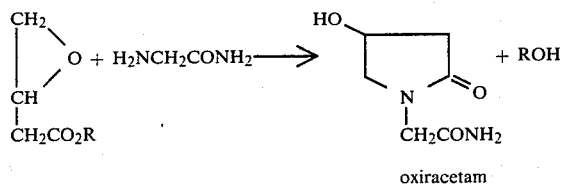

oxiracetam

The 3,4-epoxybutyric acid alkyl ester as the raw material is easily obtained, e.g. by (1) the dehydrochlorination reaction of 4-chloro-3-hydroxybutyric acid ester (J. Org. Chem., 32, 3888 (1967)) or (2) epoxidation of 3-butenoic acid ester (Japanese patent application laid-open No. Sho 60-208957/1985). The carbon number of the alkyl group is preferred to be in the range of 1 to 4.

The glycinamide used in the process of the present invention may also be used in the form of its acid salts e.g. hydrochloride, sulfate, and in this case, a base for neutralizing the acid is necessary. Examples of the base are metal alkoxides such as sodium ethoxide, alkali metal or alkaline earth metal hydroxides such as NaOH, KOH, Ca(OH)$_2$, and alkali metal carbonates such as Na$_2$CO$_3$, NaHCO$_3$, K$_2$CO$_3$, but in consideration of yield and economy, alkali metal carbonates are preferred. The quantity of glycinamide used is 1 to 1.5 equivalent based on the 3,4-epoxybutyric acid ester.

The conditions in carrying out the above reaction such as solvent, reaction temperature, reaction time, etc. are the same as those in the case of the 4-halo-3-hydroxybutyric acid alkyl ester.

[EXAMPLE]

Now, the present invention will be described more specifically below with reference to working examples.

Example 1:

In 10 ml of ethanol, 1.11 g (10 m.moles) of glycinamide hydrochloride, 1.06 g (10 m.moles) of sodium carbonate, and 1.53 g (10 m.moles) of methyl 4-chloro-3-hydroxybutyrate were stirred and refluxed simultaneously for 20 hours. After completion of the reaction, the warm reaction mixture was filtered to expel inorganic salts. The filtrate was analyzed by gas chromatography (Fluoxylate-K 1% Uniport HP 100/120, column length 0.5 m and column temperature 220° C., R$_T$ 2.8 min) (hereinafter referred to as "GC" for short). Consequently, the reaction was found to have produced oxiracetam in a yield of 75%. The filtrate was concentrated, dissolved in a small amount of water, and poured on a bed of 40 ml of Amberlite IR-120 (—SO$_3$H form) (tradename: Rohm & Haas Co.). The adsorbate was eluted with water. The eluate was fractionated, with the first and second fractions discarded and the third and following fractions were collected. The collected fractions were concentrated. The concentrate was dissolved in methanol and the solution was ice cooled ad crystallized with crystals of oxiracetam used as mother crystals. The produced crystals were collected and vaccum dried, to afford 0.55 g (yield of isolation 35%) of oxiracetam, having a melting point of 155° to 160° C. (as compared with 161° to 163° C. reported in the specification of Japanese Patent Publication Sho 58-22,034/1983).

Nuclear magnetic resonance (NMR) spectrum (CD$_3$SOCD$_3$), δ: 2.33 (2H, AB part of ABX system, J=3, 6, 17 Hz), 3.43 (2H, AB part of ABX system, J=2, 5.5, 10 Hz), 3.83 (2H, ABq, J=17 Hz), 4.34 (1H, m), 5.20 (1H, br s), 7.13 (b 1H, br s), 7.30 (1H, br s).

Example 2

In 10 ml of ethanol, 1.11 g (10 m.moles) of glycinamide hydrochloride, 1.06 g (10 m.moles) of sodium carbonate, and 1.53 g (10 m.moles) of methyl 4-chloro-3-hydroxybutyrate were stirred and refluxed simultaneously for 24 hours. The samples of resultant reaction mixture, taken 5 hours and 24 hours respectively after start of the reaction, were analyzed by GC for oxiracetam. Consequently, the yields were found to be 0% and 74% respectively.

Example 3

The same raw materials as used in Example 2 plus 50 mg of potassium iodide were stirred and refluxed simultaneously for 24 hours by following the procedure of Example 2. The samples of resultant reaction mixture, taken 4 hours, 8 hours, and 24 hours respectively after start of the reaction, were analyzed by GC for oxiracetam. Consequently, the yields were found to be 27%, 47%, and 73% respectively.

Example 4

The same raw materials as used in Example 2 plus 50 mg of sodium iodide were stirred and refluxed simultaneously for 24 hours by following the procedure of Example 2. The samples of resultant reaction mixture, taken 5 hours and 24 hours respectively after start of the reaction, were analyzed by GC for oxiracetam. Consequently, the yields were found to be 15% and 65% respectively.

Example 5

In 10 ml of water, 1.11 g (10 m.moles) of glycinamide hydrochloride, 1.06 g (10 m.moles) of sodium carbonate, and 1.53 g (10 m.moles) of methyl 4-chloro-3-hydroxybutyrate were stirred at 80° C. for 3 hours. After completion of the reaction, the resultant reaction mixture was analyzed by GC for oxiracetam. Consequently, the yield was found to be 41%.

Example 6

In 10 ml of methanol, 1.11 g (10 m.moles) of glycinamide hydrochloride, 1.06 g (10 m.moles) of sodium carbonate, and 1.53 g (10 m.moles) of methyl 4-chloro-3-hydroxybutyrate were stirred and refluxed simultaneously for 20 hours. After completion of the reaction, the resultant reaction mixture was analyzed for oxiracetam. Consequently, the yield was found to be 45%.

Example 7

In 10 ml of ethanol, 1.11 g (10 m.moles) of glycinamide hydrochloride, 1.68 g (20 m.moles) of sodium hydrogen carbonate, and 1.53 g (10 m.moles) of methyl 4-chloro-3-hydroxybutyrate were stirred and refluxed simultaneously for 21 hours. After completion of the reaction, the resultant reaction mixture was analyzed for oxiracetam. Consequently, the yield was found to be 65%.

Example 18

In 10 ml of ethanol, 1.11 g (10 m.moles) of glycinamide hydrochloride, 1.38 g (10 m.moles) of potassium carbonate, and 1.53 g (10 m.moles) of methyl 4-chloro-3-hydroxybutyrate were stirred and refluxed simultaneously for 23 hours. After completion of the reaction, the resultant reaction mixture was analyzed for oxiracetam. Consequently, the yield was found to be 40%.

Example 9

In 10 ml of ehtanol, 1.11 g (10 m.moles) of glycinamide hydrochloride, 1.06 g (10 m.moles) of sodium carbonate, and 1.67 g (10 m.moles) of ethyl 4-chloro-3-hydroxybutyrate were stirred and refluxed simultaneously for 24 hours. After completion of the reaction, the resultant reaction mixture was analyzed for oxiracetam. Consequently, the yield was found to be 64%.

Example 10

In 10 ml of 1N ethanol solution of sodium ethoxide, 1.11 g (10 m.moles) of glycinamide hydrochloride was stirred at room temperature for 1 hour. In the resultant solution, 0.53 g (5m.moles) of sodium carbonate and 1.53 g (10 m.moles) of methyl 4-chloro-3-hydroxybutyrate were refluxed for 20 hours. After completion of the reaction, the resultant reaction mixture was analyzed for oxiracetam. The yield was found to be 65%.

Example 11

In 10 ml of 1N ethanol solution of sodium hydroxide, 1.11 g (10 m.moles) of glycinamide hydrochloride was stirred at room temperature for 1 hour. In the resultant solution, 0.53 g (5 m.moles) of sodium carbonate and 1.53 g (10 m.moles) of methyl 4-chloro-3-hydroxybutyrate were refluxed for 20 hours. After completion of the reaction, the resultant reaction mixture was analyzed for oxiracetam. Consequently, the yield was found to be 60%.

Example 12

The same raw materials as used in Example 2 were stirred at 70° C. for 60 hours. After completion of the reaction, the resultant reaction mixture was analyzed for oxiracetam. Consequently, the yield was found to be 63%.

Example 13

Ethanol (10 ml) was added to glycinamide hydrochloride (1.11 g, 10 m.moles), sodium hydrogen carbonate (0.84 g, 10 m.moles) and methyl 3,4-epoxybutyrate (1.16 g, 10 m.moles), followed by heating the mixture under reflux with stirring for 23 hours, filtering off inorganic salt after the reaction, and subjecting the filtrate to GC for determination. As a result, it was found that oxiracetam was formed with a yield of 50%.

The filtrate was concentrated and dissolved in a small quantity of water, followed by loading it on Amberlite IR-120 (—SO₃H type) (10 ml), eluting with water, washing the eluate with ethyl acetate, concentrating the aqueous layer, dissolving in methanol, ice cooling, crystallizing with a crystal matrix, collecting the resulting crystals, dissolving them in water, adding active carbon for decoloration, filtering off active carbon, concentrating the filtrate, dissolving the concentrate in a small quantity of water, adding acetone, ice-cooling for crystallization, and collecting and drying the resulting crystals to obtain oxiracetam (0.39 g, isolation yield 25% in the form of white crystals.

M.P. 160°–162° C. (while 161°–163° C. according to Japanese patent publication No. Sho 58-22034/1983).

Nuclear Magnetic Resonance (NMR) spectrum (CD₃SOCD₃) δ: 2.33 (2H, AB part of ABX system, J=3, 6, 17 Hz), 3.43 (2H, AB part of ABX system, J=2, 5.5, 10 Hz), 3.83 (2H, ABq, J=17 Hz), 4.34 (1H, m), 5.20 (1H, br s), 7.13 (1H, br s), 7.30 (1H, br s).

Example 14

Ethanol (10 m) was added to glycinamide hydrochloride (1.11 g, 10 m.moles), sodium carbonate (0.54 g, 5 m.moles) and methyl 3,4-epoxybutyrate (1.16 g, 10 m.moles), followed by refluxing the mixture with stirring for 20 hours, filtering off inorganic salt after the reaction, and determining the quantity of oxiracetam by means of GC. Yield: 35%.

Example 15

Ethanol (10 ml) was added to glycinamide hydrochloride (1.11 g, 10 m.moles), sodium hydrogen carbonate (0.84 g, 10 m.moles) and isobutyl 3,4-epoxybutyrate (1.58 g, 10 m.moles), followed by refluxing the mixture with stirring for 20 hours, filtering off after the reaction and determining the quantity of oxyracetam formed. Yield: 56%.

Example 16

A 1N ethanol solution (10 ml) of sodium ethoxide was added to glycinamide hydrochloride (1.11 g, 10 m.moles), followed by stirring the mixture at room temperature for one hour, thereafter adding ethyl 3,4-epoxybutyrate (1.30 g, 10 m.moles), agitating and refluxing the mixture for 20 hours and after the reaction, determining the quantity of oxiracetam.
Yield: 45%.

Example 17

A 1N ethanol solution (10 ml) of sodium ethoxide was added to glycinamide semisulfate (1.23 g, 10 m.moles), followed by agitating the mixture at room temperature for one hour, thereafter adding methyl 3,4-epoxybutyrate (1.16 g, 10 m.moles), agitating and refluxing the mixture for 20 hours and after the reaction, determing the quantity of oxiracetam.
Yield: 40%

[EFFECT OF THE INVENTION]

In accordance with the method of the present invention, oxiracetam can be obtained by one step from readily and inexpensively available raw materials.

What we claim is:

1. A process for producing oxiracetam which comprises reacting glycineamide with a butyric acid ester in a protonic solvent or an ethereal solvent at atmospheric pressure and at a temperature between 60° C. and 160° C. for a time period between one hour and 70 hours, which butyric acid ester is expressed by the formula (I)

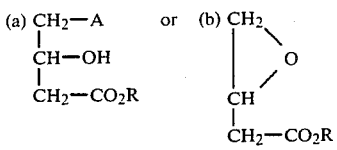

wherein A represents Cl or Br and R represents an alkyl group with 1 to 4 carbon atoms.

2. A process for producing oxiracetam as claimed in claim 1 wherein said reactants, glycineamide and butyric acid ester, are at about equimolar concentrations.

3. A process according to claim 1 wherein said butyric acid ester expressed by the formula (I) (a) is methyl 4-chloro-3-hydroxybutyrate.

4. A process according to claim 1 wherein said butyric acid ester expressed by the formula (I) (b) is methyl 3,4-epoxybutyrate or isobutyl 3,4-epoxybutyrate.

5. A process according to claim 1 wherein said glycinamide is used in the form of its acid salt.

6. A process according to claim 5 wherein said glycinamide is used in the form of its hydrochloride.

7. A process according to claim 1 wherein a base is used as a neutralizing agent for hydrogen halide which may be generated in the reaction process.

8. A process according to claim 7 wherein sodium carbonate is used as said base.

9. A process according to claim 5 wherein a base is used for liberating free glycineamide from said glycineamide in the form of its acid salt.

10. A process according to claim 9 wherein said base is an alkali metal salt.

11. A process according to claim 1 wherein said reaction solvent is a protonic solvent.

12. A process according to claim 11 wherein said protonic solvent is at least one member selected from the group consisting of water, methanol, ethanol, propanol, butanol and 2-methoxyethanol.

13. A process according to claim 1 wherein the reaction is carried out at a temperature in the range of 70° to 130° C.

14. A process according to claim 1 wherein a metal iodide is used as a catalyst in the reaction.

15. A process according to claim 14 wherein said metal iodide is at least one member selected from the group consisting of potassium iodide and sodium iodide.

* * * * *